US012636452B2

(12) United States Patent (10) Patent No.: US 12,636,452 B2
Alqarni                                (45) Date of Patent:     May 26, 2026

(54) INTUBATION SYSTEM

(71) Applicant: Imam Abdulrahman Bin Faisal University, Dammam (SA)

(72) Inventor: Abdulrahman Athwan S. Alqarni, Jubail (SA)

(73) Assignee: Imam Abdulrahman Bin Faisal University, Dammam (SA)

( * ) Notice:     Subject to any disclaimer, the term of this patent is extended or adjusted under 35 U.S.C. 154(b) by 524 days.

(21) Appl. No.: 18/315,528

(22) Filed:     May 11, 2023

(65)                Prior Publication Data

US 2024/0374851 A1     Nov. 14, 2024

(51) Int. Cl.
     *A61M 16/04*          (2006.01)
     *A61M 25/01*          (2006.01)
(52) U.S. Cl.
     CPC .... *A61M 16/0488* (2013.01); *A61M 25/0102* (2013.01); *A61M 25/0127* (2013.01)
(58) Field of Classification Search
     CPC ..... A61M 16/04–0463; A61M 16/0475–0488; A61M 25/01–0108; A61M 25/0127; A61M 2025/0166; A61M 2025/09175; A61M 2205/3317
     See application file for complete search history.

(56)                References Cited

U.S. PATENT DOCUMENTS 4,063,561 A * 12/1977 McKenna ............. A61M 16/04
                                                    128/207.15
5,257,636 A * 11/1993 White ............... A61M 25/0127
                                                    128/207.14

11,426,549 B2     8/2022 Brophy
2008/0091172 A1 *  4/2008 Toyoda .................. A61B 5/062
                                                    604/529
2010/0105984 A1 *  4/2010 Brewer ............. A61M 25/0127
                                                    600/118
2019/0388004 A1   12/2019 Victor
2022/0160209 A1 *  5/2022 Sowards ........... A61M 25/0102

FOREIGN PATENT DOCUMENTS

CN          207286429 U      5/2018
KR          10-2035711 B1   10/2019

OTHER PUBLICATIONS

Sedat Bilge, et al., "Endotracheal Intubation by Paramedics Using Neodymium Magnet and Modified Stylet in Simulated Difficult Airway: A Prospective, Randomized, Crossover Manikin Study", Emergency Medicine International, Hindawi, Article ID: 5804260, Oct. 15, 2019, 13 pages.
Muneaki Miyasaka, et al., "A Low-Cost, Point-of-Care Test for Confirmation of Nasogastric Tube Placement via Magnetic Field Tracking", Sensors, vol. 21, Issue 13, Jun. 30, 2021, pp. 1-17.

* cited by examiner

*Primary Examiner* — Rachel T Sippel
(74) *Attorney, Agent, or Firm* — Oblon, McClelland, Maier & Neustadt, L.L.P.

(57)                ABSTRACT

An intubation system is provided. The intubation system includes a metal tip bougie and a locating base. The metal tip bougie includes a bougie body with a metal tip disposed at a first end of the bougie body. The locating base includes a first magnet, a conformable base, a sensor, and an electricity port. The conformable base is disposed at a first end of the first magnet and the sensor is disposed at a second end of the first magnet. The electricity port is disposed between the first end and the second end of the first magnet. A bottom of the conformable base includes at least two runners configured to allow the locating base to slide up a neck of a patient.

20 Claims, 8 Drawing Sheets

INTUBATION SYSTEM

BACKGROUND

Technical Field

The present disclosure is directed to a medical device used for endotracheal intubation procedure, and particularly, to an intubation system for ensuring proper placement of an endotracheal tube introducer in a trachea of a patient.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In several medical scenarios, an endotracheal intubation procedure, otherwise known as an airway maintenance method or intubation method, is performed for a patient who is suffering from respiratory failure, airway obstruction or a patient who needs breathing support while the patient is under anaesthesia. During anaesthesia or in respiratory distress patients, assisted ventilation is necessary to be initiated with a minimum time delay, since hypoxia of several minutes can be fatal to most patients.

In addition, it is essential to safely perform the assisted ventilation in order to avoid causing any life-threatening complications such as aspiration pneumonia. Intubation of the trachea with an airway tube, such as an endotracheal tube and Positive Pressure Ventilation (PPV) through the endotracheal tube are common methods of ensuring oxygenation, preventing aspiration of gastric contents into the lungs, and administration of gaseous drugs. Air or oxygen may be delivered to the patient in an emergency situation through a suitably placed airway tracheal tube.

Accordingly, an intubation system including the endotracheal tube introducer is fabricated in a shape that is more or less identical to a curved structure of the human body through which the endotracheal tube passes during the intubation procedure. The endotracheal intubation procedure includes an endotracheal tube introducer, which is otherwise known as a bougie, for intubating an endotracheal tube into the trachea. The positioning of the bougie correctly into the trachea must be done quickly to avoid any brain injury to the patient. During the intubation procedure, the bougie is intubated into the trachea through the mouth and then through the oral cavity.

In some situations including patients with difficult airways and those at high risk for aspiration, the procedure becomes more challenging. While using conventional methods of endotracheal intubation, several issues such as accidental insertion of the bougie into the esophagus, or insertion of the bougie at the incorrect distance, are faced. Furthermore, the time involved for x-ray confirmation for accurate positioning of the bougie may lead to several complications, especially in a patient suffering from pneumothorax. Moreover, at some healthcare centres, no such provisions are provided.

U.S. Ser. No. 11/426,549 describes an apparatus for assisting proper placement of an endotracheal tube during patient intubation. An arcuate formed at bottom surface of an external member is superposed on a patient's neck during intubation. The external member includes a proximity sensor and a magnet. An insertion member is movably coupled to an end member which includes a proximity tag member and a magnet member. The magnet member is configured to be attracted to the magnet to guide the endotracheal tube to the correct location. However, the external member is devoid of any means for efficient maneuvering of the external member over the patient's neck.

CN207286429 describes a conduit which includes a catheter body, a magnet, a power supply, a sensor, a data processor, and an alarm. A metalwork is embedded with a tip of the catheter body. The sensor is arranged between the magnet and an infant suprasternal notch. An input terminal of the data processor is connected with the sensor, and an output terminal is connected with the alarm. When attraction between the magnet and the metalwork reaches maximum, i.e., the distance between the magnet and the metalwork is minimum, the tip of the catheter body reaches desired position. Having several components for the intubation makes the procedure complex.

The embodiments disclosed herein have an objective to provide a simple and compact intubation system which gives more control and manipulation during the endotracheal intubation. It is also an objective of the present disclosure to develop an efficient intubation system which can be fabricated with less complexity and a tip of a bougie that can be controlled externally for efficient maneuvering into the patient's trachea through quick actions by a medicine practitioner and avoiding putting the patient at risk for aspiration pneumonia or any brain injury.

Accordingly, a need exists for an efficient intubation system with an external control over the tip of the bougie. The embodiments herein provide an intubation system with an external magnetic control over the tip of the bougie. In addition, the system embodiments herein exploit the benefits of using a sensor for tracking the real-time position of the tip of the bougie which is further used to efficiently guide the bougie into the trachea using the external magnetic control device. Unlike existing intubation systems, the present disclosure has a simple and compact external system for efficient maneuvering of the bougie. The embodiments herein are directed to such a need.

SUMMARY

In an exemplary embodiment, an intubation system is described. The intubation system includes a metal tip bougie and a locating base. The metal tip bougie includes a bougie body with a metal tip disposed at a first end of the bougie body. The locating base includes a first magnet, a conformable base, a sensor, a notch, and an electricity port. The conformable base is disposed at a first end of the first magnet and the sensor is disposed at a second end of the first magnet. The notch is disposed at a first end of the sensor The electricity port is disposed between the first end of the first magnet and the second end of the first magnet. A bottom of the conformable base includes at least two runners configured to allow the locating base to slide on a neck of a patient. A magnetic force generated by the first magnet of the locating base is configured to guide the metal tip bougie during an intubation process. The sensor of the locating base is configured to measure the closeness of the metal tip of the metal tip bougie to the first magnet of the locating base during the intubation process.

In some embodiments, each runner of the conformable base is connected to the first magnet via one or more vertical attachment columns. In some embodiments, the vertical attachment columns are fabricated at least one material selected from a rubber, a polyvinyl chloride (PVC), a polytetrafluoroethylene, a Teflon, a plastic polymer, and a non-thermoplastic material.

In some embodiments, each runner is connected to the first magnet by at least three vertical attachment columns.

In some embodiments, the bougie body is fabricated of at least one material selected from a rubber, a polyvinyl chloride (PVC), a polytetrafluoroethylene, a Teflon, a plastic polymer, and a non-thermoplastic material.

In some embodiments, at least two runners are fabricated of at least one material selected from a rubber, a polyvinyl chloride (PVC), a polytetrafluoroethylene, a Teflon, a plastic polymer, and a non-thermoplastic material.

In some embodiments, the conformable base is fabricated of at least one material selected from a rubber, a polyvinyl chloride (PVC), a polytetrafluoroethylene, a Teflon, a plastic polymer, and a non-thermoplastic material.

In some embodiments, the sensor includes a metal sensor tip that is fabricated of a different metal than the metal tip. In some embodiments, the sensor includes a metal sensor tip that is fabricated of a same metal as the metal tip.

In some embodiments, a length of the runner is equal to a length of the vertical attachment columns. In some embodiments, the length of the runner is from 1.1 up to 1.3 times greater than the length of the vertical attachment column. In some embodiments, the length of the vertical attachment columns is from 1.1 up to 1.3 times greater than the length of the runner.

In some embodiments, the metal tip is fabricated of at least one selected from the group consisting of stainless steel, iron, copper, tin, aluminum, and a combination thereof.

In some embodiments, the first magnet is at least one selected from an electromagnet and a permanent magnet.

In some embodiments, the at least two runners and the vertical attachment columns have a cylindrical cross section. In some embodiments, a diameter of an individual runner is from 1.5 up to 2.5 times greater than a diameter of an individual vertical attachment column.

In some embodiments, the notch is configured to perform a maneuver on the neck of the patient.

In some embodiments, a pair of wheels is disposed between the bottom surface of the first magnet and the top surface of the conformable base configured to move the first magnet horizontally on the conformable base.

In some embodiments, the conformable base further includes a depression configured to hold the first magnet. In some embodiments, the depression is substantially rectangular. In some embodiments, an area of the conformable base is from 1.4 to 1.9 times greater than an area of the depression. In some embodiments, the depression contains a second magnet configured to hold the first magnet in the depression.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
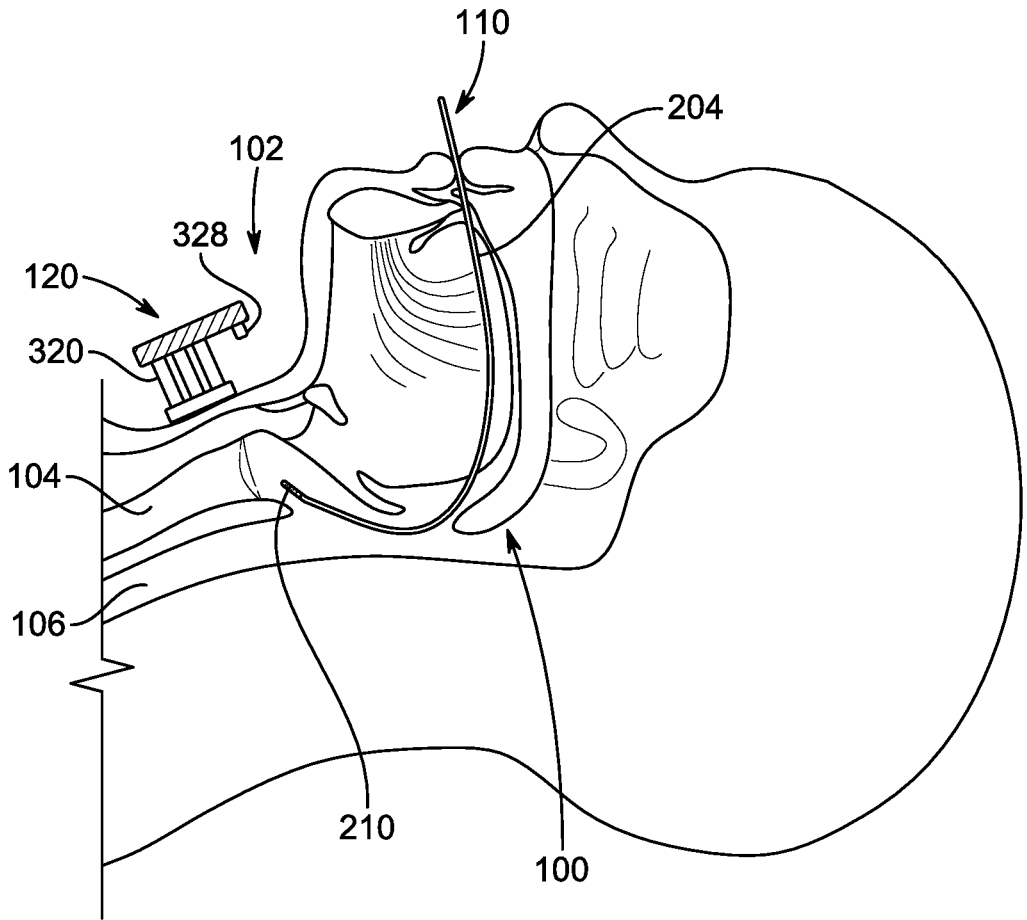
FIG. 1 is a schematic sectional view of a pharyngeal region of a subject that undergoes tracheal intubation procedure using an intubation system, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

Aspects of the present disclosure are directed to an intubation system for facilitating proper placement of an endotracheal tube introducer into a trachea of a patient using efficient magnetic forces and sensing methods during an endotracheal intubation procedure. The present embodiments disclose an intubation system which provide more control and manipulation during a endotracheal intubation procedure.

During the intubation procedure, first an endotracheal tube introducer is intubated into the trachea through the mouth and then through the oral cavity, then an endotracheal tube is inserted through it. Accordingly, the endotracheal tube introducer is fabricated in a shape that is identical to a curved structure of the human body through which the endotracheal tube passes during the intubation procedure. The endotracheal tube introducer is otherwise referred to as the bougie, which means the bougie is inserted into the airway first, then an endotracheal tube is railroaded over the bougie into the airway, after which the bougie is removed for intubating the endotracheal tube into the trachea. The endotracheal tube provides oxygen and inhaled gases to the lungs and protects the lungs from contamination, such as gastric contents or blood. Furthermore, the insertion of the endotracheal tube inside the trachea maintains an open airway or serves as a conduit through which to administer certain drugs and gases.

The embodiments disclosed herein, use efficient magnetic forces and sensing methods during an endotracheal intubation procedure to insert the bougie into a trachea of a patient. As used herein, the term 'endotracheal intubation procedure' refers to the medical procedure in which an endotracheal tube introducer is inserted into the trachea through an oral cavity of the patient. As used herein, the term 'bougie' refers to an endotracheal tube introducer generally fabricated as a curved structure and using a flexible material, such as rubber, polyvinyl chloride (PVC), polytetrafluoroethylene, Teflon, any plastic polymer, a non-thermoplastic material such as silicone, or any other suitable material.

The bougie is placed between the vocal cords through the trachea. The bougie includes an elongated body having a distal end configured to be placed in the trachea of the patient and a proximal end to hold the bougie during the placement. The elongated body is substantially cylindrical or circular in shape or any other shape known in the art. It is generally, but not limited to, fabricated in a length of 50 cm up to 100 cm, preferably in 60 cm, or 70 cm or 90 cm. The structure of the bougie is fabricated in different lengths based on the patient. A bougie is generally fabricated in different lengths for use in pediatric and adult intubation procedures. Generally, for pediatric intubation procedures, the length of the bougie is selected to be between 50 cm and 60 cm; and generally, for adult intubation procedures, the length of the bougie is selected to be between 60 cm and 100 cm.

The intubation system disclosed herein includes an endotracheal tube introducer and an external locating body. The endotracheal tube introducer as disclosed herein is a metal tip bougie, wherein the bougie includes a metal tip disposed at its distal end. This metal tip of the metal tip bougie is tracked and guided using the external locating body. The length of the metal tip is generally about 10% the length of the bougie body. In some embodiments, the length of the metal tip may be more or may be less than the length of the bougie body. The distal end has a bend at an angle to include the metal tip. The metal tip is generally fabricated using a metallic material such as, for example, cobalt, neodymium, gadolinium, dysprosium, holmium, nickel, silver, and stainless steel.

The external locating body refers to a locating base. The locating base includes a conformable base, a magnet, and a sensor. The magnet of the locating base is configured to attract a metal tip of the metal tip bougie to guide the metal tip bougie to the correct position in the trachea. The other components of the locating base are configured to position the locating base on the neck of the patient and to allow a user to slide the locating base in a direction appropriate to guide the metal tip of the metal tip bougie towards the trachea of the patient.

The sensor of the locating base is configured to sense the closeness of the of the metal tip bougie to the magnet. Sensing the position of the metal tip is further used to understand if the positioning of the locating base needs to be changed to further adjust the distance between the magnet of the locating base and the metal tip to efficiently guide the metal tip of the metal tip bougie. The sensor is positioned near the magnet, either directly connected to it or connected to a part of the locating base which holds the magnet.

The conformable base refers to the part of the external locating body to which the other parts of the locating base, such as, for example, the magnet, are connected to. Mainly, the conformable base is configured to rest the locating base on the neck of the patient and include vertical attachments and runners. The vertical attachments are generally cylindrical in shape. These vertical attachments have a curved structure, or a straight structure. The vertical attachments connect the magnet to runners. The runners rest on the neck of the patient and can slide in an upward or downward direction on the neck of the patient. The runners allow the movement of the locating base in a direction in which the metal tip of the bougie needs to be moved. The runners are also generally of a cylindrical shape.

The task of intubation becomes more challenging in emergent situations, patients with difficult airways and those that are at elevated risk for aspiration or have airway abnormalities, which make intubation difficult. Intubation difficulties are often associated with obesity, pregnancy, facial trauma/abnormalities, short and thick neck, laryngeal edema, and the like. When such abnormalities are associated with a decrease in breath reserve volume, an increase in magnetic force is necessary to attract the metal tip bougie. For such scenarios, electricity is utilized to increase the strength of the magnetic forces of the magnet. In addition to other components, the locating base includes an electricity port for emergent situations. The present disclosure uses magnetic forces of a magnet and sensing capabilities of a sensor to perform the endotracheal intubation procedure with high rate of success.

Referring to FIG. 1, a schematic sectional view of a pharyngeal region 100 of a subject that undergoes an endotracheal intubation procedure using an intubation system 102 is illustrated, according to an embodiment of the present disclosure. As used herein, the term 'pharyngeal region 100' refers to the hollow passage inside neck that starts behind a nose and ends at the top of a trachea 104 and an esophagus 106. In the present disclosure, the subject is a mammal, especially a human. In some embodiments, the subject may be an animal. Hereinafter, the term 'human' may be interchangeably referred to as 'the patient.'

In the present disclosure, the endotracheal intubation procedure is performed utilizing the intubation system 102 including a metal tip bougie 110 and a locating base 120. The insertion of the metal tip bougie 110 may be done under direct visualization (using a laryngoscope) or indirect visualization (such as rigid fiberoptic laryngoscopy and rigid video laryngoscopy). As used herein, the term 'laryngoscope' refers to the device that is used to visualize the larynx and adjacent structure mainly for inserting the endotracheal tube into the tracheobronchial tree. Human manipulation is necessary during the insertion process.

A user or practitioner inserts the metal tip bougie 110 into the oral cavity of the patient. Further, the metal tip bougie 110 is swept to the patient's midline, keeping the tongue on one side, for example, on the left side, to bring the epiglottis into view. The metal tip bougie 110 is then advanced until the metal tip bougie 110 reaches an angle between a base of the tongue and the epiglottis. Further, the metal tip bougie 110 is lifted upward (depending on the position of the user or the practitioner) but more importantly towards the chest and away from the nose to bring the vocal cords into view.

In the present disclosure, the lifting of a tip of the metal tip bougie 110 is magnetically done using a magnet on the locating base 120. In the embodiments disclosed herein, the locating base 120 comprises one or more runners that rest on the neck of the patient. These one or more runners are used to move the locating base about the neck of the patient. The one or more runners are attached to the magnet through one or more vertical attachments 320.

A sensor 328 connected to the magnet senses the position of the metal tip 210 of the bougie 110. The sensor monitors the closeness of the metal tip to the magnet. If the magnet and the metal tip are not close enough, the locating base 120 is moved accordingly. In some embodiments, the sensor 328 has a metal sensor tip facing towards the skin surface. In some embodiments, the metal sensor tip may be movably coupled to the sensor 328 such that a distance between the metal sensor tip and the skin surface of the patient may be adjusted based on age and skin size of the patient for desired sensing capability. In an embodiment, the metal sensor tip is fabricated of a different metal than the metal tip 210 of the metal tip bougie 110. In an alternate embodiment, the metal sensor tip is fabricated of a same metal as the metal tip 210 of the metal tip bougie 110. The metal refers to one from a group of metals including stainless steel, iron, copper, tin, aluminum, and a combination thereof. In some embodiments, the metal refers to a material selected from cobalt, neodymium, gadolinium, dysprosium, holmium, nickel, or silver.

The runners and the one or more vertical attachments 320 are biased towards a first end of the magnet and the sensor 328 is biased towards the second end of the magnet. The biasing of the placement of the components at the first end and the second end of the magnet is to permit ease of adjust of the position of the locating base 120 on the neck of a subject. The sensor 328 biased on the second end of the magnet with no other component such as the vertical attachments or the runners between the sensor 328 and the neck of the patient provides a clear path for sensing the metal tip 210 of the metal tip bougie 110. This clear path of sensing provides instantaneous manual feedback which further provides the user or medicine practitioner feedback on efficiently maneuvering the locating base 120 to guide the metal tip bougie 110.

Preferably, the vertical attachments 320 all connect to the same ½ portion of the magnet measured along a length of the magnet parallel to the runners from the first end of the magnet. The sensor is preferably position within ¼ of the length of the magnet from the second end of the magnet, along the central axis of the magnet or at a left or right edge. Arranged in this way a physician can easily manipulate the position of the sensor, for example the distance between sensor and the skin surface of the patient's neck, by tilting the magnet upwards and downwards in a plane parallel to the runners.

Once the metal tip of the metal tip bougie 110 is positioned correctly inside the trachea 104, an endotracheal tube is inserted into the mouth via the metal tip bougie 110 and through the vocal cords to the point where an expandable cuff of the endotracheal tube is slightly posterior the vocal cords and the expandable cuff is then inflated to snugly fix the endotracheal tube with the trachea 104 of the patient.

Figure 2:
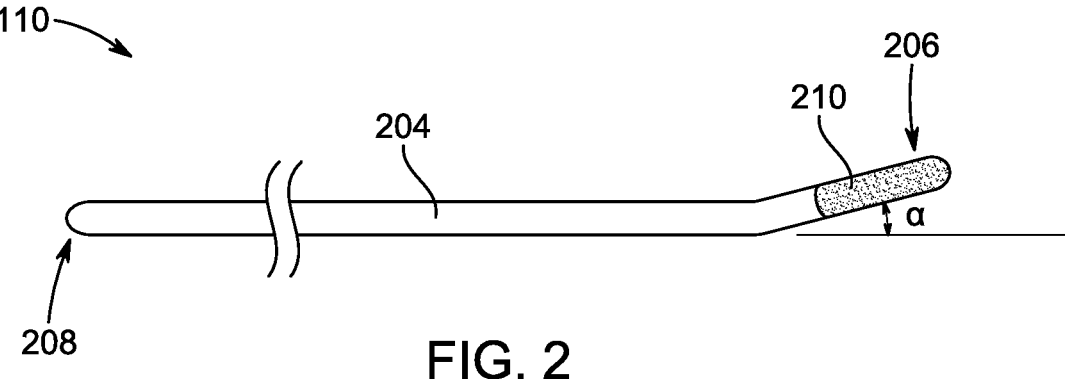
FIG. 2 is a schematic perspective view of a metal tip bougie of the intubation system of FIG. 1, according to certain embodiments.

Referring to FIG. 2, a schematic perspective view of the metal tip bougie 110 of the intubation system 102 is illustrated, according to an embodiment of the present disclosure. The metal tip bougie 110 includes a bougie body 204, otherwise known as 'an elongated body 204', including a distal end 206 and a proximal end 208. The user inserts the metal tip bougie 110 into the oral cavity of the patient by holding the proximal end 208 of the metal tip bougie 110. The bougie body 204 including the proximal end 208 is substantially elliptical. The bougie body 204 including the proximal end 208 of the bougie body 204 may also be spherical, or any other shape known in the art. The bougie body 204 may be fabricated from a flexible material such as rubber, plastic polymer, polytetrafluoroethylene, Teflon™, a non-thermoplastic material such as silicone, and a metal. In the present disclosure, the bougie body 204 is fabricated of polyvinyl chloride (PVC). The bougie body 204 is generally fabricated in pediatric and adult sizes. The length of the bougie body is generally, but not necessarily between 50 cm and 100 cm, preferably 60 cm, or 70 cm, or 90 cm. Generally, the pediatric bougie body length being between 50 cm and 60 cm; and the adult bougie body length being between 60 cm and 100 cm.

The bougie body 204 includes a metal tip 210 disposed at the distal end 206 thereof. Generally, the length of the metal tip is about 10% the length of the bougie body 204. In some embodiments, the length of the metal tip is more than 10% the length of the bougie body, up to 25% the length of the bougie body. In some embodiments, the length of the metal tip is less than 10% the length of the bougie body. In the present disclosure, the metal tip 210 and the bougie body 204 may be an integral component. In some embodiments, the metal tip 210 may be detachably attached to the bougie body 204. In one embodiment, the metal tip 210 may be snap-fitted to the bougie body 204 at the first end 206 thereof. The metal tip 210 may be rigidly attached to the bougie body 204 to form a single body. The metal tip 210 is configured to bend at an angle 'α' relative to the bougie body 204. The angle 'α' defined between a longitudinal axis of the bougie body 204 and a longitudinal axis of the metal tip 210 is alternatively referred to as the metal tip angle 'α'.

In an embodiment, the metal tip angle 'α' may be varied manually using an adjustment mechanism attached to the bougie body 204 or due to the inherent elastic property of the material of the bougie body 204. Particularly, the bougie body 204 may be made up of flexible biodegradable and biocompatible PVC material such that the metal tip 210 can regain its original position thereof after manipulation. In the present disclosure, the metal tip 210 is fabricated of at least one selected from the group comprising of stainless steel, iron, copper, tin, aluminum, and a combination thereof. In some embodiments, the metal tip 210 may be made up of a magnetic material such as cobalt, neodymium, gadolinium, dysprosium, holmium, and nickel. In some embodiments, the metal tip 210 may be fabricated with a non-magnetic material such as silver, and stainless steel. Further, the metal tip 210 may be made lighter than the bougie body 204 for easy maneuvering during the endotracheal intubation procedure. In some embodiments, the body of the metal tip 210 is solid and rigid. In some embodiments, the body of the metal tip 210 is semi-rigid.

Figure 3:
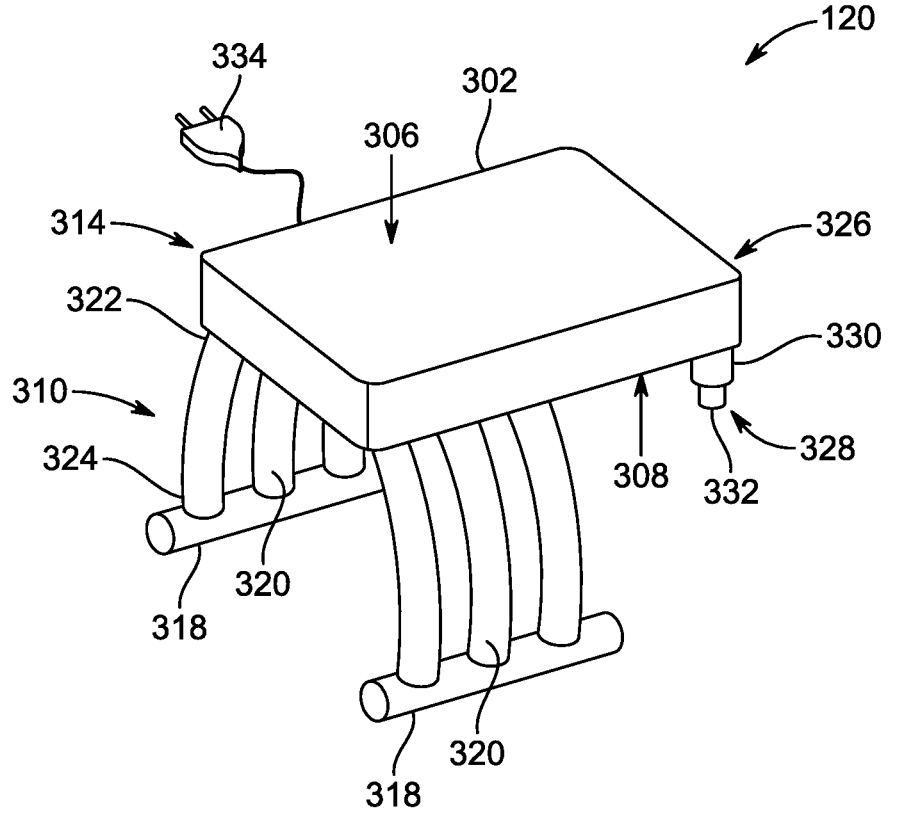
FIG. 3 is a schematic perspective view of a locating base of the intubation system of FIG. 1, according to one embodiment.

Referring to FIG. 3, a schematic perspective view of the locating base 120 of the intubation system 102 is illustrated, according to an embodiment of the present disclosure. During the endotracheal intubation procedure, the locating base 120 is positioned on the neck of the patient and the metal tip bougie 110 is inserted through the oral cavity of the patient. The locating base 120 includes a first magnet 302 configured to attract the metal tip 210 of the metal tip bougie 110 as the metal tip 210 advances through the oral cavity such that the metal tip 210 of the metal tip bougie 110 attracts towards the first magnet 302 and enters the trachea 104 of the patient. The first magnet 302 may have a rectangular shape. In some embodiments, the shape of the first magnet 302 may be, but are not limited to, square, circular, rhombic, or a polygon. In one of the embodiments disclosed herein, the first magnet 302 is a permanent magnet. The first magnet 302 is generally made of a ferromagnetic material, a paramagnetic material, and a diamagnetic material. In some embodiments, the first magnet 302 is an electromagnet. As used herein, the term 'electromagnet' refers to the type of magnet in which the magnetic field is produced by an electric current. In general, electromagnets include a wire wound into a coil around a core made of iron. The electric current flowing through the wire creates a magnetic field which is concentrated in the center of the coil. In some embodiments, the first magnet 302 has an elongated body having a top surface 306 and a bottom surface 308.

The locating base 120 further includes a conformable base 310 having a top attached to the first magnet 302. In some embodiments, the conformable base 310 may be disposed at a first end 314 of the first magnet 302. The conformable base 310 is configured to allow the locating base 120 to slide up or down the neck of the patient. The conformable base 310 may be made up of a skin barrier layer, for example, over-molded with silicone, so that the conformable base 310 may be easily affixed in position against the skin surface. The conformable base 310 is also fabricated of flexible material, such as rubber, polyvinyl chloride (PVC), polytetrafluoroethylene, Teflon, any plastic polymer, a non-thermoplastic material such as silicone, or any other suitable material.

Furthermore, a bottom of the conformable base 310 includes at least two runners 318 configured to allow the locating base 120 to slide up or down the neck of the patient. In an embodiment, the two or more runners 318 may be rigidly attached to the conformable base 310 to form a single body. In an alternate embodiment, the two or more runners 318 may be detachably attached to the conformable base 310 using a press fit, a snap fit, or fastening members. In the present disclosure, the two or more runners are fabricated of flexible material such as, for example, rubber, polyvinyl chloride (PVC), polytetrafluoroethylene, Teflon, any plastic polymer, a non-thermoplastic material such as silicone, or any other suitable material.

In the present disclosure, the two or more runners 318 have a cylindrical cross section that have a length and defines a constant diameter along the length. In some embodiments, the two or more runners have the cylindrical cross section with a varying diameter along the length of the runners. In some embodiments, the two or more runners 318 may have a cross section that may facilitate rolling over the skin surface of the patient. In some embodiments, the two or more runners 318 may include wheels or rollers to allow sliding of the locating base 120 over the skin surface of the patient.

Each runner 318 of the conformable base 310 is connected to the first magnet 302 via one or more vertical attachment columns 320. Particularly, each of the two or more runners 318 may be attached to the bottom surface 308 of the first magnet 302 via the one or more vertical attachment columns 320. Each vertical attachment column 320 may have a top end 322 configured to couple with the bottom surface 308 of the first magnet 302 and a bottom end 324 configured to couple with the runner 318. The vertical attachment column 320 may have a length extending between the top end 322 and the bottom end 324 thereof. In some embodiments, the vertical attachment columns 320 may be evenly distributed along each of the runners 318. In some embodiments, the vertical attachment columns 320 may be biased towards one end of each of the runners 318. Further, the vertical attachment columns 320 have a cylindrical cross section defining a diameter. In some embodiments, the vertical attachment columns 320 may have a rectangular cross section, a square cross section, a triangular cross section, an elliptical cross section, or any other polygon cross section. In an embodiment of the present disclosure, the at least two runners 318 and the vertical attachment columns 320 may have different cross sections. In some embodiments of the present disclosure, the one or more vertical attachments columns 320 have a curved structure. The curved structure of the vertical attachment columns 320 supports the at least two runners to slide up or down the neck of the patient, for the first magnet 302 to guide the metal tip 210 of the metal tip bougie 110. In some embodiments, the structure of the vertical attachment columns 320 may be straight or of any suitable configuration to appropriately support the first magnet. In some embodiments, the runners 318 may be attached to the first end 314 of the first magnet 302. In another embodiment, the runners 318 may be attached midway or in between the first end 314 and a second end 326 of the first magnet 302. In some embodiments, the vertical attachment columns 320 may be attached to the bottom surface of the first magnet. In a different embodiment of the present disclosure, the vertical attachment columns 320 may be attached to a component connected to the first magnet and holding the first magnet.

Each runner 318 is connected to the first magnet 302 by one or more vertical attachment columns 320. In one embodiment, each runner 318 is connected to the first magnet 302 by at least three vertical attachment columns. Each vertical attachment columns 320 of an embodiment are of the same structure. In some embodiments, each of the vertical attachment columns 320 may be of a different structure. In one embodiment, the length of the runner 318 is equal to the length of the vertical attachment columns 320. In another embodiment, the length of the runner 318 is from 1.1 to 1.3, more preferably 1.15 to 1.25, times greater than the length of the vertical attachment column 320. In some embodiments, the length of the vertical attachment column 320 is from 1.1 to 1.3, more preferably 1.15 to 1.25, times greater than the length of the runner 318. In some embodiments, the diameter of an individual runner 318 is from 1.5 to 2.5, more preferably 1.8 to 2.3, and more preferably 2.1 to 2.25, times greater than the diameter of an individual vertical attachment column 320. The at least two runners 318 and the vertical attachment columns 320 are also fabricated of a flexible material, such as rubber, polyvinyl chloride (PVC), polytetrafluoroethylene, Teflon, any plastic polymer, a non-thermoplastic material such as silicone, or any other suitable material. In an implementation of the present disclosure, the vertical attachment columns 320 may constitute the conformable base 310 and the runners 318 may be separately attached to the conformable base 310. In another implementation, the vertical attachment columns 320 and the runners 318 may together constitute the conformable base 310.

The locating base 120 further includes a sensor 328 disposed at the bottom surface 308 of the first magnet 302. Particularly, the sensor 328 may be disposed at the second end 326 of the first magnet 302. In some embodiments, the sensor 328 may be disposed at one corner of the second end 326 of the first magnet 302. In some embodiment, the sensor 328 may be disposed at the center of the second end 326 of the first magnet 302. In an embodiment, the sensor 328 may include a sensor body 330 attached to the first magnet 302 and a metal sensor tip 332 attached to the sensor body 330 and facing towards the skin surface. In some embodiments, the sensor body 330 may be an integral component of the first magnet 302. In some embodiments, the sensor body 330 may be detachably attached to the first magnet 302. In such an embodiment, the sensor 328 may be attached at a required position on the second end 326 of the first magnet 302 to achieve most efficient feedback from the sensor about the closeness of the metal tip bougie 110 and the first magnet 302. In some embodiments, the metal sensor tip 332 may be movably coupled to the sensor body 330 such that a distance between the metal sensor tip 332 and the skin surface of the patient may be adjusted based on age and skin size of the patient for desired sensing capability. For an instance wherein the sensor needs to be adjusted closer to the patient's neck, the locating base 120 might be pressed towards the neck of the patient, the flexible material such as, for example, PVC used for the fabrication of the conformable base 310, the one or more vertical attachments 320 and each of the runners 318 allows the sensor 328 and the first magnet 302 to be positioned closer to the neck of the patient. The conformable base 310, the one or more vertical attachments 320 and each of the runners 318 are biased on one end of the first magnet 302 with the sensor 328 on the other end to allow such an adjustment. With no component placed in the path between the sensor 328 and the neck of the patient, the sensing is more accurate and the instantaneous manual feedback from the sensor 328 allows the locating base 120 to be maneuvered appropriately to guide the metal tip bougie 110 using the first magnet 302. In an embodiment, the metal sensor tip 332 is fabricated of a different metal than the metal tip 210 of the metal tip bougie 110. In an alternate embodiment, the metal sensor tip 332 is fabricated of a same metal as the metal tip 210 of the metal tip bougie 110.

In one example, the sensor 328 may be a radio frequency sensor. In another example, the sensor 328 may be a proximity sensor. As used herein, the term 'proximity sensing' refers to the ability of a sensor to detect the presence of nearby objects without any physical contact. In some examples, the sensor 328 may be a magnetic sensor or a metal sensor. As used herein, the terms 'magnetic sensor' and 'metal sensor' refers to the sensor 328 which detects a position of the metal tip 210 of the metal tip bougie 110 made up of the magnetic material or the non-magnetic material, respectively.

In some embodiments, the sensor 328 may be a standalone device which may be superposed on the neck of the patient. In such a case, one or more sensors may be positioned at various locations of the neck of the patient. In some embodiments, one or more sensors may be positioned at various locations of the first magnet 302. The sensor 328 may detect only if the metal tip 210 of the metal tip bougie 110 is correctly positioned inside the trachea 104 of the patient. The sensor 328 may not detect if the metal tip 210 resides in the esophagus 106. In some embodiments, the sensor 328 may be an ultra-sound imaging device which may scan the position of the metal tip 210 and display the same on an interface of a smart device (such as a smart phone, a smart watch, smart glasses, tablets, and phablets) of the user. In an embodiment, the sensor 328 may be replaced by the ultra-sound imaging device. In an alternate embodiment, the ultra-sound imaging device may be additionally present with the sensor 328. In some embodiments, the locating base 120 may include an audio indicator for the confirmation of proper location of the metal tip 210 within the trachea 104. The audio indicator may include an audio alarm. The alarm may produce a sound to notify the user regarding the position of the metal tip 210. In some embodiments, the locating base 120 may include a visual indicator for the confirmation of proper location of the metal tip 210. The visual indicator may include blinking of light emitting diodes (LEDs), change in color of the LEDs, turning on/off the LEDs to notify the user.

The locating base 120 further includes an electricity port 334 disposed between the first end 314 of the first magnet 302 and the second end 326 of the first magnet 302. The electricity port 334 is configured to couple with an electric source. In one embodiment, the electric source may be a battery. In another embodiment, the electric source may be a commercial power distribution line. The electricity port 334 is further configured to establish an electric communication between the electric source and the first magnet 302. In case of the electromagnet, the electric port is communicated with the wire wound into the coil around the core to produce magnetic field. The magnetic field of the first magnet 302 is varied by varying the power supply, and particularly, ampere rating of the current can be controlled to vary a strength of the magnetic field. Such capability of the first magnet 302 allows the intubation system 102 to be used for patients of any age or skin size. In an example, during the endotracheal intubation procedure, depending on a distance between the first magnet 302 and the metal tip 210, the power supply can be controlled to increase or decrease the magnetic field. It is to be noted that the power supply to the electricity port 334 may be a conventional alternating current (AC) or direct current (DC) which is configured to provide the desired power to operate the first magnet 302 of the intubation system 102.

Figure 4:
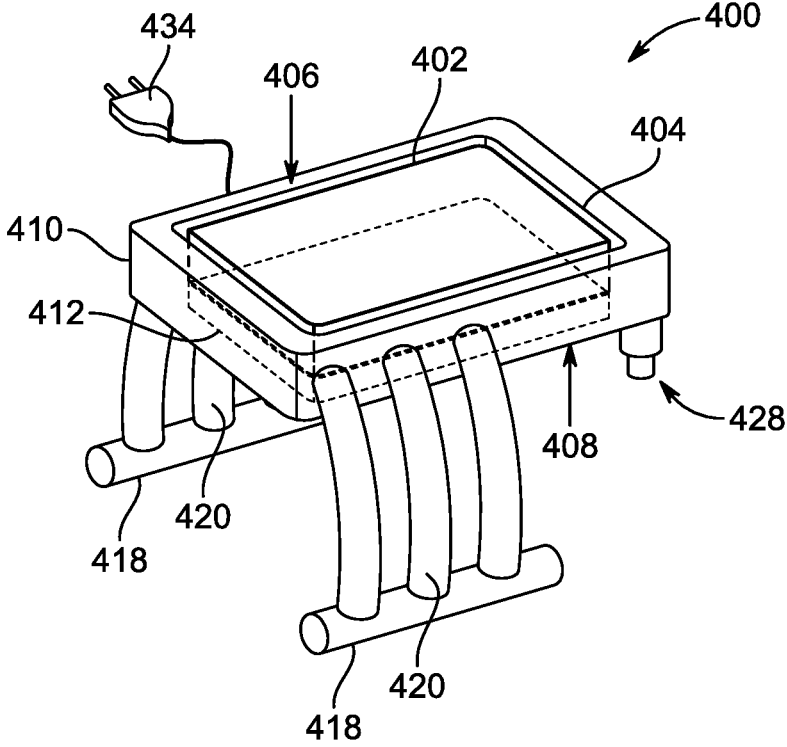
FIG. 4 is a schematic perspective view of a locating base, according to another embodiment.

Referring to FIG. 4, a schematic perspective view of a locating base 400 is illustrated, according to an embodiment of the present disclosure. The locating base 400 includes a conformable base 410 configured to support a first magnet 402. In the present disclosure, the conformable base 410 includes a depression 404 configured to hold the first magnet 402. In an embodiment, the conformable base 410 may be a rectangular body having a volume greater than a volume of the first magnet 402 which is in rectangular shape such that the first magnet 402 can be disposed within the depression 404 defined in the conformable base 410. The depression 404 is substantially rectangular to accommodate the first magnet 402 having the rectangular shape. In some embodiments, the conformable base 410 has a body shape from the group including, but not limited to, a square, a circular, a rhombic, or a polygon. Accordingly, the shape of the first magnet 402 also has a shape including, but not limited to, a square, a circular, a rhombic, or a polygon. In such embodiments. The depression 404 defined in the conformable base 410 is also selected from, but not limited to, a square, a circular, a rhombic, or a polygon, to accommodate the first magnet 402 having a certain shape. In the embodiments disclosed, the body shape of the conformable base 410 may be same as the shape of the first magnet 402 and the shape of the depression 404 defined in the conformable base 410 to accommodate the first magnet 402. In certain embodiments, the shape of the conformable base 410 might be different from the shape of the first magnet 402 and the shape of the depression 404 defined in the conformable base 410. The shape of the depression 404 is configured to accommodate the shape of the first magnet 402.

A volume defined by the depression 404 may be greater than or equal to the volume of the first magnet 402 as such the first magnet 402 may be freely and snugly fit within the depression 404. In one embodiment, the depression 404 may be defined at a top surface 406 of the conformable base 410. In such a case, an area, otherwise known as a surface area, of the top surface 406 of the conformable base 410 is 1.4 to 1.9 times greater than an area of the depression 404 defined in the top surface 406 of the conformable base 410. In some embodiments, the area of the conformable base 410 is from 1.5 to 1.8, and more preferably 1.6 to 1.7, times greater than the area of the depression 404. Further, the depression 404 contains a second magnet 412 configured to hold the first magnet 402 in the depression 404. The shape of the second magnet 412 is selected from, but not limited to, a rectangle, a square, a circular, a rhombic, or a polygon. In some embodiments, the shape of the second magnet 412 may be same as the first magnet 402. In certain embodiments, the shape of the second magnet 412 may be different than the first magnet 402 but configured to hold the first magnet 402. In one embodiment, the second magnet 412 may be a permanent magnet. In another embodiment, the second magnet 412 may be an electromagnet. In some embodiments, a depth of the depression 404 may be equal to a sum of thickness of each of the first magnet 402 and the second magnet 412 such that the first and second magnets 402, 412 may be received within the depression 404. In an alternate embodiment, the depression 404 may be present in a bottom surface 408 of the conformable base 410 as described above with reference to the top surface 406. In some embodiments, the depression 404 may be defined as conical, spherical, cubical, and rhombical in conformance with a shape and size of the first magnet 402.

In some embodiments, the locating base 400 may further include at least two runners 418 attached to the conformable base 410 and one or more vertical attachment columns 420 attaching the runners 418 to the conformable base 410. The structure of the one or more vertical attachment columns 420 may be curved to support the conformable base holding the first magnet 402 and the second magnet 412 in it. In some embodiments, the structure of the one or more vertical attachment columns 420 may be configured straight. The conformable base 410 may function as a supporting body to support the first magnet 402 and sensors 428 may be mounted on the conformable base 410. The sensors 428 may be biased at one end of the first magnet 402 and the runners 418 and the vertical attachment columns 420 may be biased towards the other end of the first magnet 402. Further, an electricity port 434 may be defined in the conformable base 410 to communicate with the first magnet 402 in certain embodiments, such that the first magnet 402 is an electromagnet. In such embodiments, the electricity port 434 allows the user to alter the magnetic power of the first magnet 402 to efficiently guide the metal tip of the metal tip bougie. Such a locating base 400 is configured to guide a metal tip bougie as described in FIG. 2 into the trachea of a patient. The embodiments of the locating base described in FIG. 3 work and function as the embodiments described in FIG. 4 with a metal tip bougie as described in FIG. 2.

Figure 5:
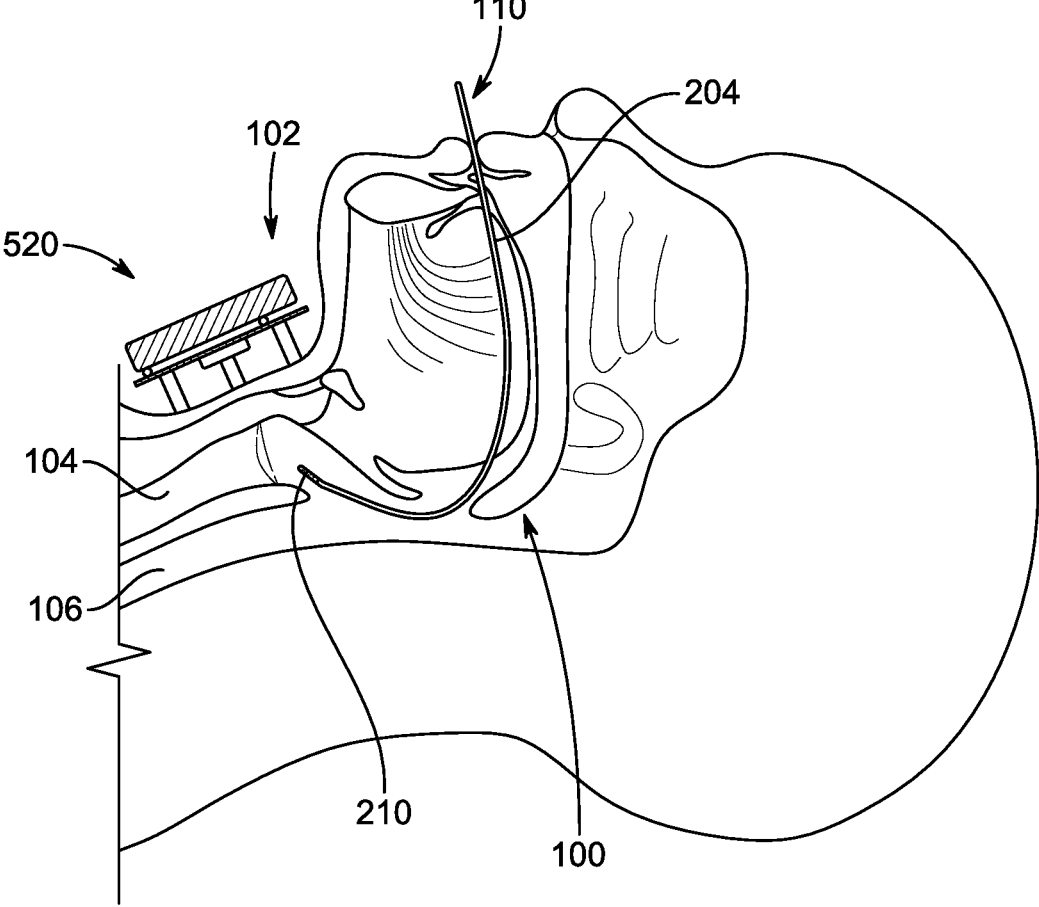
FIG. 5 is a schematic sectional view of a pharyngeal region of a subject that undergoes tracheal intubation procedure using an intubation system, according to one embodiment.

Referring to FIG. 5, a schematic sectional view of a pharyngeal region 100 of a subject that undergoes an endotracheal intubation procedure using an intubation system 102 is illustrated, according to another embodiment of the present disclosure. In the current embodiment of the present disclosure, the locating base 520 of the intubation system 102 in FIG. 5 includes extended locating base holders. In some scenarios of performing intubation process, patients might not be fully sedated or hypnotized, in which case they might move causing the locating base to fall. In some scenarios, such as treating a pediatric patient, there can be difficulty placing the locating base on the neck. For such scenarios, an extended holder for the locating base 520 is beneficial to place the locating base around the neck of the patient.

In the embodiments herein, the vertical attachment columns of the locating base 520 are extended in length in combination with the curved structure of the vertical attachment columns. The curved structure of the vertical attachment columns is identical to the curved structure of the neck. This identical curved structure in combination with the extended length of the vertical attachment columns allows the locating base 520 to be placed around the neck of the patient such that the vertical attachment columns lie around the neck and the conformable base is centered on the neck as shown in FIG. 5. Through such a placement of the locating base, the movement of the patient will not cause the locating base to fall, or a pediatric patient will not have to carry the weight of the locating base. This provides more stability to the positioning of the locating base 520 of the intubation system 102.

Figure 6:
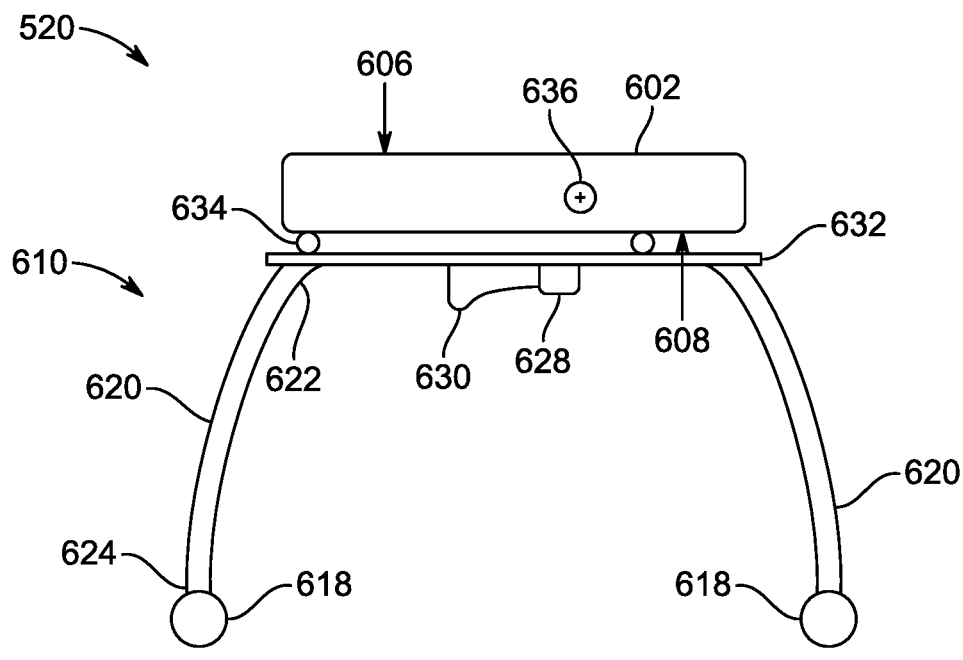
FIG. 6 is a schematic perspective view of a locating base of the intubation system of FIG. 5, according to one embodiment.
Figure 7:
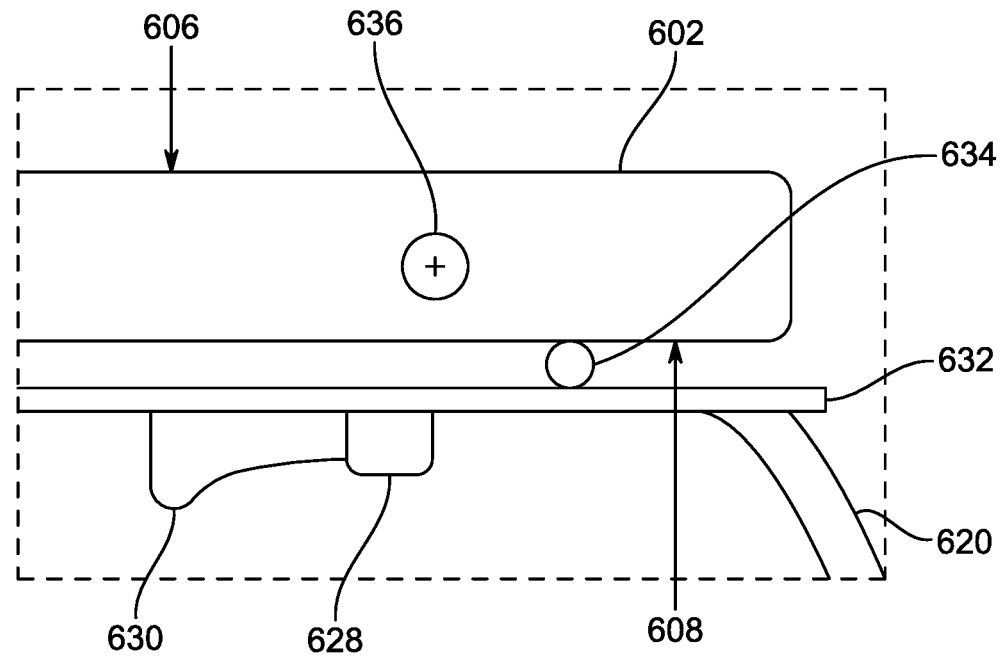
FIG. 7 is an enlarged view of a part of the schematic perspective view of a locating base of FIG. 6.

Referring to FIG. 6, a schematic perspective view of the locating base 520 of the intubation system 102 is illustrated, according to an embodiment of the present disclosure. During the endotracheal intubation procedure, the locating base 520 is placed around the neck of the patient with the magnet 502 centered on the neck of the patient. In an embodiment of the present disclosure, the conformable base 632 includes at least a pair of wheels 634 up to two pairs of wheels. The pair of wheels 634 roll along the bottom surface 608 of the magnet 602 and top surface of the conformable base 632 as shown in FIG. 6. As the sensor 628 reads the distance between the magnet 602 and the tip of the metal tip bougie, and as this distance changes with the movement of the metal tip bougie, the magnet 602 needs to be readjusted to be close enough to the metal tip bougie. The pair of wheels 634 aid to slide the magnet 602 as shown in FIG. 6 and FIG. 7. The magnet 602 can be moved towards the chin of the patient or towards the chest of the patient, such that the closeness between the magnet 602 and the tip of the metal tip bougie is increased or maintained in order to further guide the moving metal tip bougie. The pair of wheels 634 can also be a metallic ball on which the magnet 602 can roll.

Figure 9:
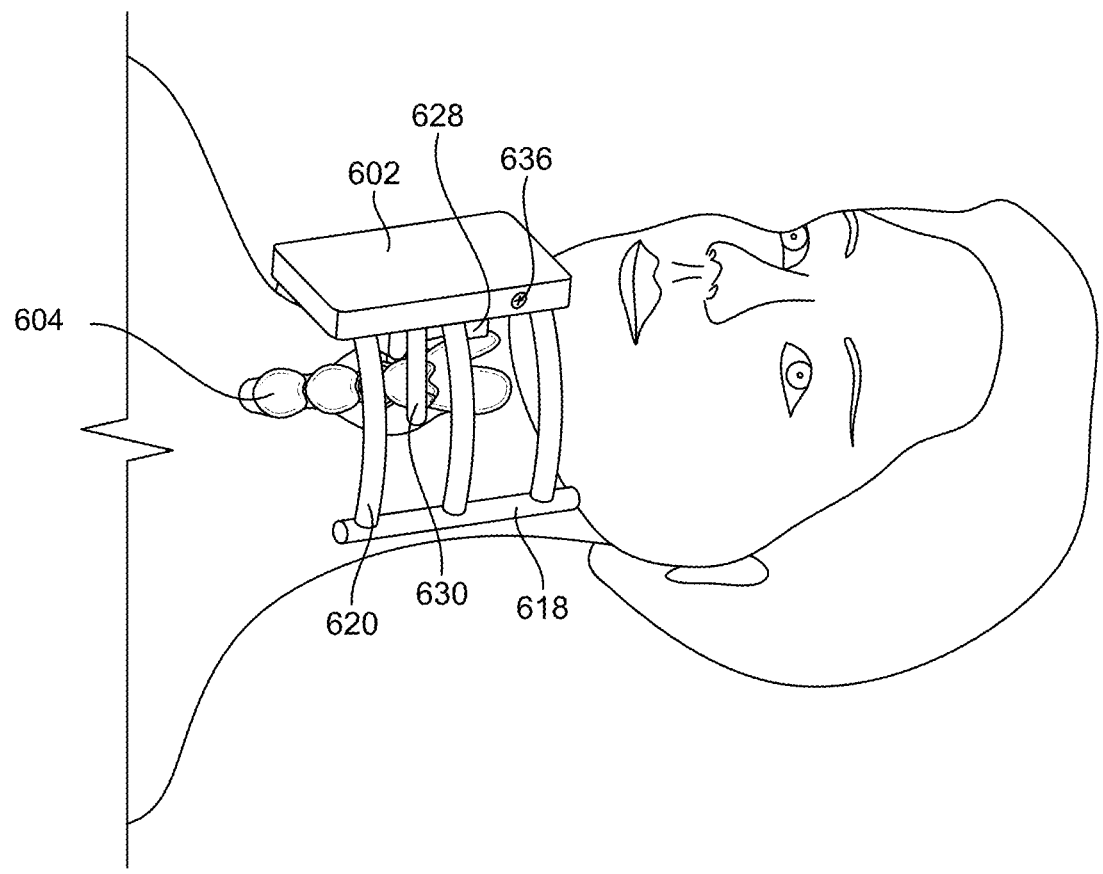
FIG. 9 is a schematic perspective view of the locating base of FIG. 6 positioned on the neck of a subject that undergoes tracheal intubation procedure using an intubation system, according to one embodiment.

In the embodiments herein, the vertical attachment columns 620 of the locating base 520 are extended in length in combination with the curved structure of the vertical attachment columns 620. The curved structure of the vertical attachment columns 620 is identical to the curved structure of the neck. This identical curved structure in combination with the extended length of the vertical attachment columns allows the locating base 520 to be placed around the neck of the patient such that the vertical attachment columns lie around the neck and the conformable base is centered on the neck as shown in FIG. 9. Through such a placement of the locating base, the movement of the patient will not cause the locating base to fall, or a pediatric patient will not have to carry the weight of the locating base. This provides more stability to the positioning of the locating base 520 of the intubation system 102.

In certain scenarios, during endotracheal intubation, a maneuver is most often used to help align the airway structures called a Sellick Maneuver. The Sellick Maneuver is performed by applying gentle pressure to the anterior neck (in a posterior direction) at the level of the Cricoid Cartilage. In an embodiment of the present disclosure, the schematic view of the locating base 520 in FIG. 6, includes a mark 636 on the magnet 602 to indicate the placement of the locating base 520 above the thyroid cartilage of the patient. Locating base 520 in FIG. 6 also shows a notch 630 placed next to the sensor 628 on the bottom surface of the conformable base 632, such that the sensor 628 is facing the patient's chest direction on the locating base 520 and the notch 630 is towards the patient's trachea above the cricoid cartilage. The structure of the notch 630 is such that it is enlarged on one end as compared to the other end as shown in enlarge image in FIG. 7. The end of the notch 630 against the sensor 628 is smaller and the other end is enlarged. This notch aids in performing the Sellick Maneuver.

Figure 8:
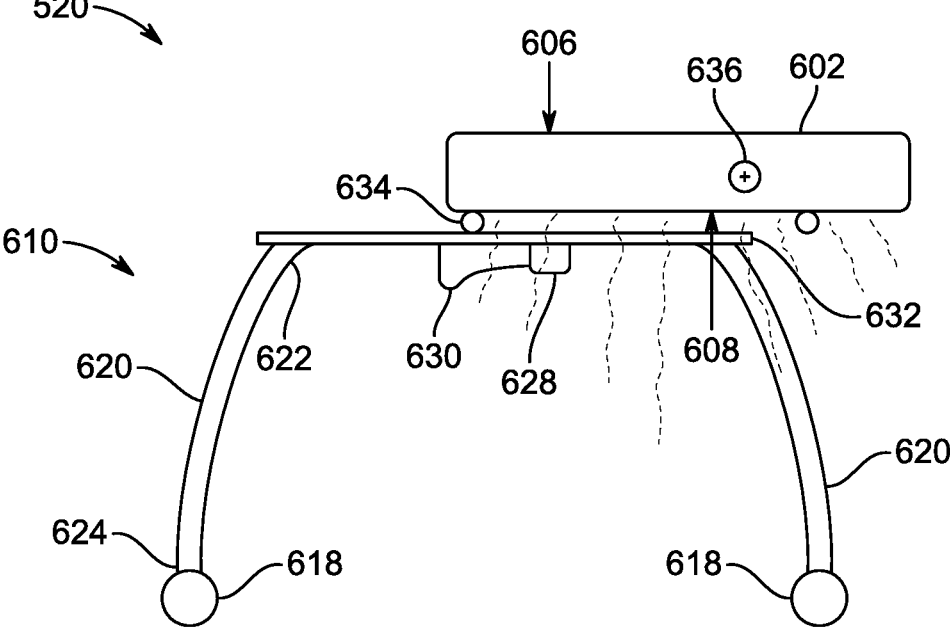
FIG. 8 is a schematic perspective view of the locating base of the intubation system of FIG. 5, according to another embodiment.

In this embodiment of the present disclosure, the notch 630 and the sensor 628 are fixed in position under the conformable base 632. When it is required to increase the closeness between the magnet 602 and the metal tip of the metal tip bougie, the locating base 520 is moved. If the sensor 628 is not fixed in position, the relative distance between the sensor 628 and the metal tip bougie will be disturbed on moving the locating base 520. Having the sensor 628 and notch 630 fixed in position, such a movement of the locating base 520 will not affect the readings from the sensor 628 and cause no disturbance in detecting the metal tip of the metal tip bougie. As shown in FIG. 8, moving the magnet 602 to increase or maintain the closeness between the magnet 602 and the metal tip of the moving metal tip bougie, will not disturb the sensor 628 and notch 630 when they are fixed in position. The magnitude of the magnetic field of the magnet 602 is central and can achieve the required closeness with the metal tip of the metal tip bougie as the magnet 602 is moved with the help of the pair of wheels 634.

Figure 10:
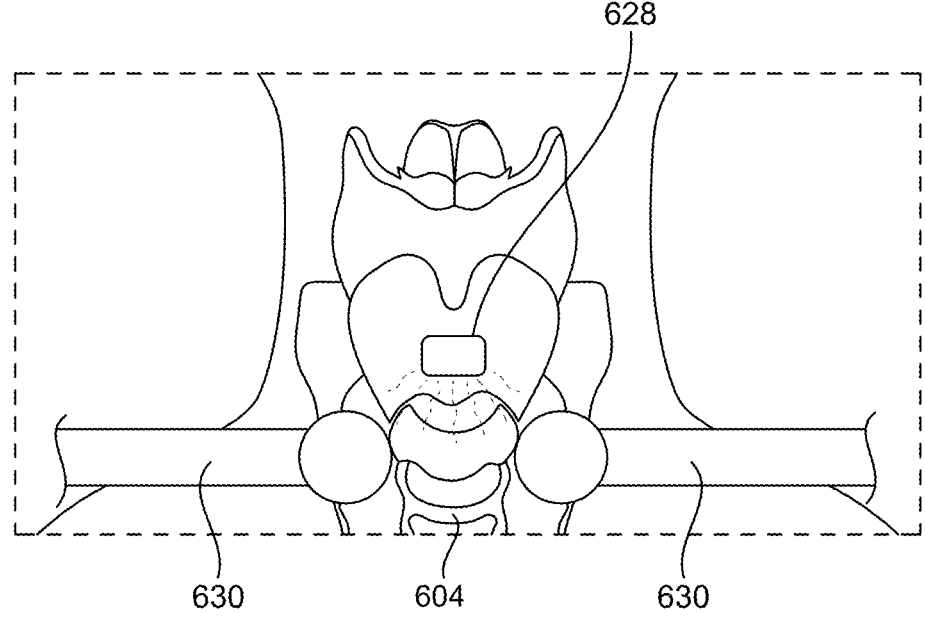
FIG. 10 is a schematic sectional view of the locating base of FIG. 6 performing a maneuver on a subject, according to one embodiment.

Referring to FIG. 9, a schematic sectional view of a subject that undergoes an endotracheal intubation procedure using an intubation system 102 is illustrated, according to another embodiment of the present disclosure. In the embodiments herein, it is to be noted that the notch 630 at the bottom surface of the conformable base of the locating base 520 is placed above the cricoid cartilage 604 using the mark 636 on the magnet 602. The notch 630 can also have two parallel vertical columns instead of the enlarged end of the notch 630 as described above in FIG. 6 and FIG. 7. Such a structure of the notch 630 in combination with the placement as shown in FIG. 9, aids in performing the Sellick maneuver. To perform the Sellick maneuver, the locating base 520 is pressed downwards towards the patient's trachea. The two parallel vertical columns of the notch 630 aid in applying gentle pressure on the patient's neck to align the airway structures of the patient. The sensor 628 also achieves a clear path for reading the closeness between the magnet 602 and the metal tip of the bougie, from between the two parallel vertical columns of the notch 630. Referring to FIG. 10, the two parallel vertical columns of the notch 630 of the locating base 520 are observed performing the Sellick maneuver. The two columns 630 apply pressure on two sides of the cricoid cartilage 604 to align the airway structure of the patient during the intubation process.

The present disclosure provides the intubation system which is simple and compact. Furthermore, the components required to fabricate the intubation system are easily available and cost effective. Moreover, the presence of the electromagnet in the intubation system allows the user to alter the magnetic power of the magnet as per the requirements with the use of the electricity port. The sensor only detects when the metal tip of the metal tip bougie is present inside the trachea of the patient. Furthermore, the materials used to manufacture the metal tip bougie allows easy maneuvering of the metal tip bougie inside the pharyngeal region to further internal parts of the patients till the metal tip reaches the correct position of the trachea. The intubation system is devoid of an external source for examining the position of the metal tip inside the trachea of the patient.

Numerous modifications and variations of the present disclosure are possible in light of the above teachings. It is therefore to be understood that within the scope of the appended claims, the invention may be practiced otherwise than as specifically described herein.

The invention claimed is:

1. An intubation system, comprising:
a metal tip bougie and a locating base;
wherein the metal tip bougie includes a bougie body with a metal tip disposed at a first end of the bougie body;
wherein the locating base includes a first magnet, a conformable base, a sensor, a protrusion, and an electricity port;
wherein the conformable base is disposed at a first end of the first magnet and the sensor is disposed at a second end of the first magnet;
wherein the protrusion is disposed at a first end of the sensor;
wherein the electricity port is disposed between the first end of the first magnet and the second end of the first magnet;
wherein a bottom of the conformable base comprises at least two runners configured to allow the locating base to slide on a neck of a patient;
wherein a magnetic force generated by the first magnet of the locating base is configured to guide the metal tip of the metal tip bougie during an intubation process; and
wherein the sensor of the locating base is configured to measure a closeness of the metal tip of the metal tip bougie to the first magnet of the locating base during the intubation process.

2. The intubation system of claim 1, wherein each runner of the at least two runners of the conformable base is connected to the first magnet via one or more vertical attachment columns.

3. The intubation system of claim 1, wherein the bougie body is fabricated of at least one material selected from a rubber, a polyvinyl chloride (PVC), a polytetrafluoroethylene, a Teflon, a plastic polymer, and a non-thermoplastic material.

4. The intubation system of claim 1, wherein the metal tip is fabricated of at least one material selected from a stainless steel, an iron, a copper, a tin, an aluminum, a cobalt, a neodymium, a gadolinium, a dysprosium, a holmium, a nickel, a silver, and a combination of two or more of the at least one material.

5. The intubation system of claim 1, wherein the conformable base is fabricated of at least one material selected from a rubber, a polyvinyl chloride (PVC), a polytetrafluoroethylene, a Teflon, a plastic polymer, and a non-thermoplastic material.

6. The intubation system of claim 1, the at least two runners are fabricated of at least one material selected from a rubber, a polyvinyl chloride (PVC), a polytetrafluoroethylene, a Teflon, a plastic polymer, and a non-thermoplastic material.

7. The intubation system of claim 2, wherein the one or more vertical attachment columns are fabricated of at least one material selected from the group consisting of a stainless steel, an iron, a copper, a tin, an aluminum, and a combination thereof.

8. The intubation system of claim 1, wherein the sensor further comprises a metal sensor tip.

9. The intubation system of claim 8, wherein the metal sensor tip is fabricated of a material different than the metal tip.

10. The intubation system of claim 8, wherein the metal sensor tip is fabricated of a material that is the same as the metal tip.

11. The intubation system of claim 2, wherein a length of each of the runners is from 1 up to 1.3 times greater than a length of the one or more vertical attachment columns.

12. The intubation system of claim 2, wherein a length of the one or more vertical attachment columns is from 1 up to 1.3 times greater than a length of the at least two runners.

13. The intubation system of claim 1, wherein the first magnet is at least one selected from an electromagnet and a permanent magnet.

14. The intubation system of claim 1, wherein the at least two runners are configured with a cylindrical cross section.

15. The intubation system of claim 2, wherein the one or more vertical attachment columns are configured with a cylindrical cross section.

16. The intubation system of claim 2, wherein a diameter of an individual runner of the at least two runners is from 1.5 to up 2.5 times greater than a diameter of an individual vertical attachment column of the one or more vertical attachment columns.

17. The intubation system of claim 1, wherein the protrusion is configured to perform a maneuver on the neck of the patient.

18. The intubation system of claim 1, wherein a pair of wheels is disposed between a bottom surface of the first magnet and a top surface of the conformable base configured to move the first magnet horizontally on the conformable base.

19. The intubation system of claim 1, wherein the conformable base further comprises a depression configured to hold the first magnet.

20. The intubation system of claim 19, wherein the depression contains a second magnet configured to hold the first magnet in the depression.

\* \* \* \* \*